(12) United States Patent
Schembri

(10) Patent No.: US 6,773,676 B2
(45) Date of Patent: Aug. 10, 2004

(54) DEVICES FOR PERFORMING ARRAY HYBRIDIZATION ASSAYS AND METHODS OF USING THE SAME

(75) Inventor: Carol T. Schembri, San Mateo, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 408 days.

(21) Appl. No.: 09/884,792

(22) Filed: Jun. 19, 2001

(65) Prior Publication Data

US 2001/0046702 A1 Nov. 29, 2001

Related U.S. Application Data

(63) Continuation-in-part of application No. 09/299,976, filed on Apr. 27, 1999, now Pat. No. 6,261,523.

(51) Int. Cl.[7] .................................................. B01L 3/00
(52) U.S. Cl. .................... 422/102; 422/104; 435/287.2; 435/288.3; 435/305.1
(58) Field of Search .............................. 422/102, 104; 435/287.2, 288.3, 305.1

(56) References Cited

U.S. PATENT DOCUMENTS

| | | | |
|---|---|---|---|
| 5,061,448 A | * | 10/1991 | Mahe et al. .................. 422/99 |
| 5,100,775 A | * | 3/1992 | Smyczek et al. .............. 435/6 |
| 5,552,087 A | | 9/1996 | Zeheb et al. |
| 5,595,707 A | | 1/1997 | Copeland et al. |
| 5,650,327 A | | 7/1997 | Copeland et al. |
| 5,654,199 A | | 8/1997 | Copeland et al. |
| 5,654,200 A | | 8/1997 | Copeland et al. |
| 5,710,043 A | * | 1/1998 | Pay .......................... 435/297.5 |
| 5,744,096 A | * | 4/1998 | Jones et al. .................... 422/58 |
| 5,958,760 A | | 9/1999 | Freeman |
| 6,114,122 A | | 9/2000 | Besemer et al. |
| 6,238,910 B1 | | 5/2001 | Custance et al. |

OTHER PUBLICATIONS www.genomicsolutions.com/products/bio/hyb.html "GeneTAC Hybridization Station", Tuesday, Apr. 10, 2001 www.genonics.com/training/faqs/hyb–faq.html. "Hybridization Station FAQ" Tuesday, Apr. 10, 2001.
www.ventanadiscovery.com/poster.n\html. C. Wolfe et al. "Fully–automated Kinetic–mode Hybridization of Microarray Glass Slides" Apr. 10, 2001.
www.affymetric.com/products/ins–fluid–content.html "Genechip Instrument Systems", Apr. 10, 2001.
www.apbiotech.com/applicaiton/microarray/homepage.htm "Microarrays", Apr. 10, 2001.

* cited by examiner

Primary Examiner—Jan M. Ludlow

(57) ABSTRACT

Array hybridization devices and methods for their use are provided. The subject devices are characterized by having a substantially planar bottom surface, a cover, at least one fluid port and at least one adjustable spacing element for adjusting the spacing between an array and the bottom surface. In using the subject devices, an array is placed on the at least one adjustable spacing element in the chamber and the space between the array and the bottom surface is adjusted by moving the at least one adjustable spacing element. The adjusted array is contacted with at least one biological sample introduced into the chamber. The subject inventions find use in a variety of array-based applications, including nucleic acid array hybridizations.

31 Claims, 4 Drawing Sheets

Figure 1:
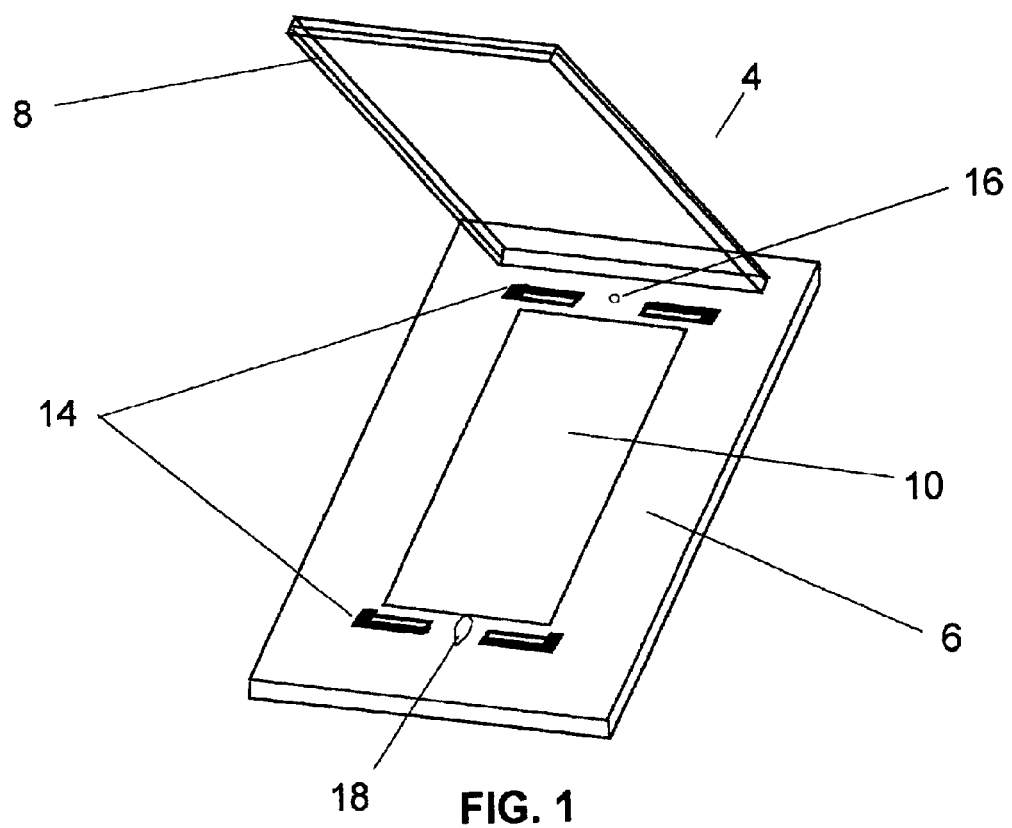

DEVICES FOR PERFORMING ARRAY HYBRIDIZATION ASSAYS AND METHODS OF USING THE SAME

CROSS REFERENCE TO RELATED APPLICATIONS

This application is a continuation in part of application Ser. No. 09/299,976 filed Apr. 27, 1999, now U.S. Pat. No. 6,261,523; the disclosure of which is herein incorporated by reference.

FIELD OF THE INVENTION

The field of this invention is biopolymeric arrays.

BACKGROUND OF THE INVENTION

"Biochips" or arrays of binding agents, such as oligonucleotides, cDNA and peptides, and the like have become an increasingly important tool in the biotechnology industry and related fields. These binding agent arrays, in which a plurality of binding agents are deposited onto a solid support surface in the form of an array or pattern, find use in a variety of applications, including gene expression analysis, drug screening, nucleic acid sequencing, mutation analysis, and the like.

In array-based assays in which an array of binding agents is employed, the array is typically contacted with a fluid sample that is suspected of containing the analyte(s) of interest. After a sufficient incubation period with the sample, often at elevated temperatures, the array is typically washed with at least one wash agent to remove the unbound sample from the array and any material that may have non-specifically bound to the array surface. As such, array based procedures typically require a number of different steps including fluid introduction, incubation, washing, etc.

In array hybridization procedures, it is critical that the sample is evenly applied across the array and that the array does not dry out during the hybridization process, as such drying-out can damage the array.

Initially, array based hybridizations simply took place on a microscope slide, typically the slides were covered with a cover slip to help distribute the sample over the array surface and keep the slide from drying out. However, this method was labor-intensive and inefficient. To address these problems, hybridization chambers were developed to simplify the process and increase the efficiency thereof. Such chambers range from a simple chamber which merely functions as a depository for the array during hybridization to chambers that have some or all of the hybridization process automated.

For example, U.S. Pat. No. 6,114,122 discloses an automated hybridization station having a fluid delivery system associated with it. The '122 patent discloses a package for housing an array during hybridization where the array substrate is attached to the body of the cartridge, preferably with an adhesive. Also, U.S. Pat. No. 5,958,760 discloses an automated apparatus having a chamber which uses a silicon rubber gasket or O-ring to substantially seal the chamber for processing a glass slide support therein. Further, U.S. Pat. No. 5,595,707 discloses an automated biological reaction apparatus having a carousel slide support which supports a plurality of slide supports thereon to increase the quantity of slides which can be processed concurrently. The '707 patent further discloses that the biochemical reaction is carried out under a layer of an evaporation inhibiting liquid to minimize dehydration.

Although effective, there are drawbacks associated with each of the above techniques. For example, sealing means such as adhesives, gaskets or O-rings used in the process may result in a flawed array surface or unreacted sections of the array due to the adhesive, gasket or O-ring contacting the array and interfering with the even distribution of the sample over the array surface. Similarly, use of an evaporation inhibiting liquid may create an un-even distribution of the liquid causing evaporation of portions of the array and ultimately un-reacted sections. In addition, the device disclosed in the '122 patent is limited in that it must be used with specific array formats, and therefore is not suitable for use with all of the different array platforms currently employed by those of skill in the art.

As such, there is continued interest in the development of new devices for array-based hybridizations and methods of using the same. Of particular interest would be the development of an array-based hybridization chamber, and methods of use thereof, that provides for the even distribution of a sample over an array surface, substantially prevents dehydration of the array surface during the hybridization process, is simple to use, efficient, at least partially automated and can be used with the multitude of different array formats currently employed in the art.

Relevant Literature

Patents and patent applications of interest include: U.S. Pat. Nos. 5,552,087; 5,595,707; 5,650,327; 5,654,199; 5,654,200; 5,958,760; 6,114,122; and 6,238,910.

Also of interest are the webspaces located at the URLs of the world wide web which are at agilent.com; affymetrix.com; apbiotech.com and genomicsolutions.com.

SUMMARY OF THE INVENTION

Array hybridization devices and methods for their use are provided. The subject devices are characterized by having a substantially planar bottom surface, a cover, at least one fluid port and at least one adjustable spacing element for adjusting the spacing between an array and the bottom surface. In using the subject devices, an array is placed on the at least one adjustable spacing element in the chamber and the space between the array and the bottom surface is adjusted by moving the at least one adjustable spacing element. The adjusted array is contacted with at least one biological sample introduced into the chamber. The subject inventions find use in a variety of array-based applications, including nucleic acid array hybridizations.

BRIEF DESCRIPTIONS OF THE DRAWINGS

FIG. 1 provides a representation of a hybridization chamber of the present invention.

Figure 2:
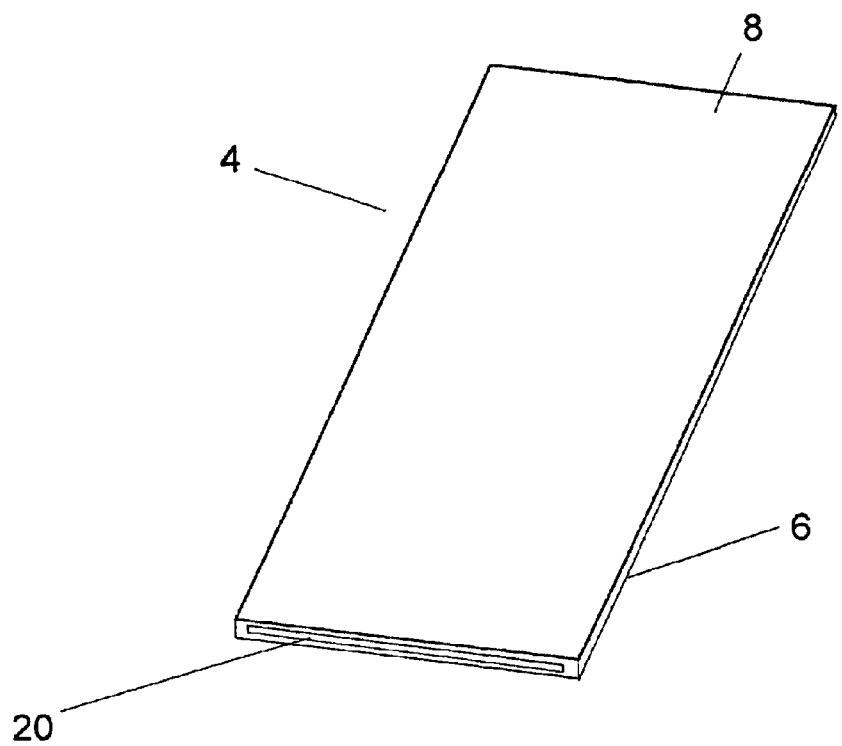

FIG. 2 provides a representation of an embodiment of a hybridization chamber of the present invention where the chamber is one unit.

Figure 3:
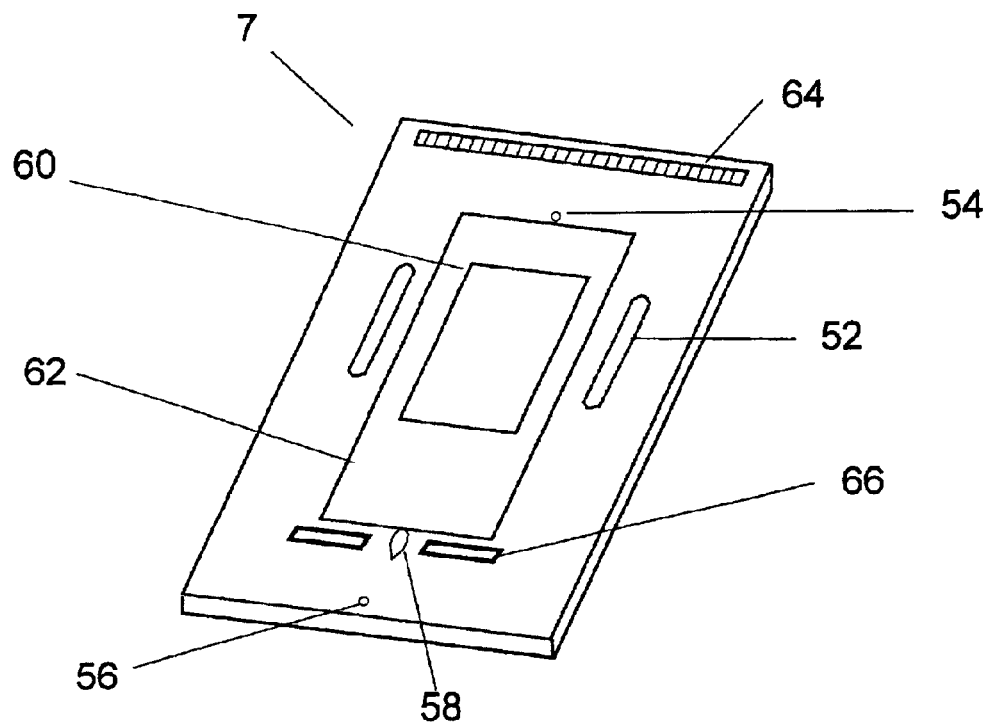

FIG. 3 provides a representation of a substantially planar bottom surface of the present invention.

Figure 4:
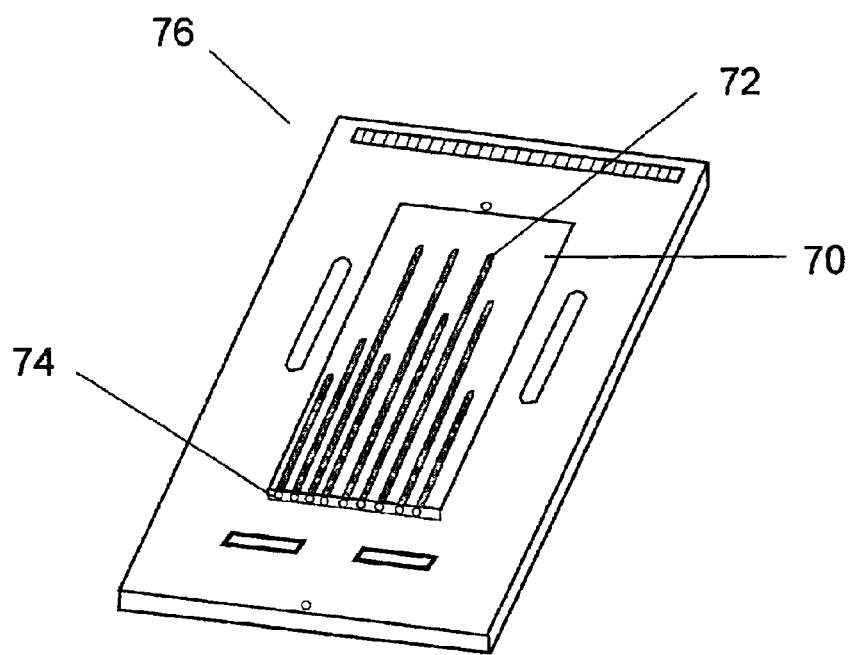

FIG. 4 provides a representation of an embodiment of a substantially planar bottom surface of the present invention having micro-channels.

Figure 5:
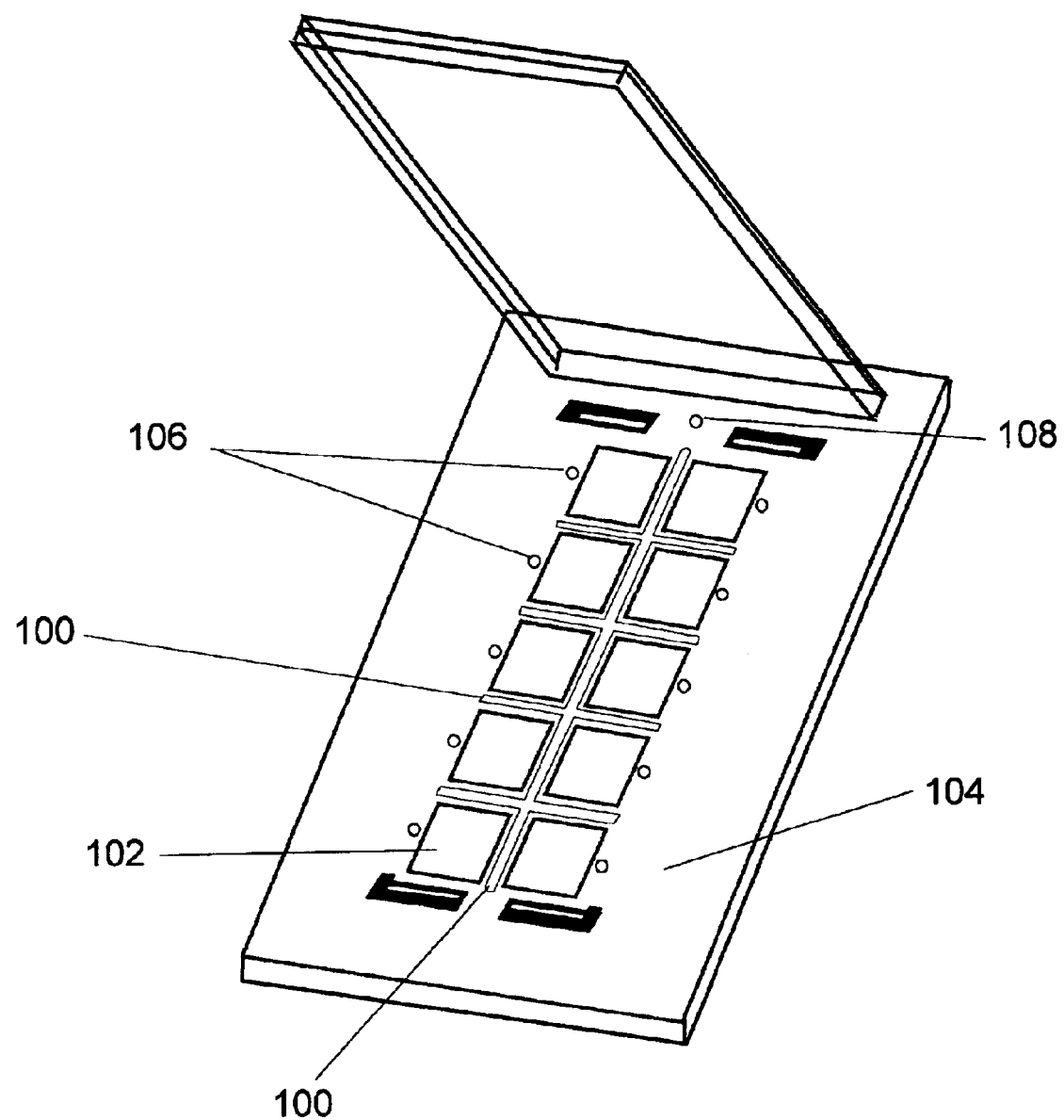

FIG. 5 provides a representation of an embodiment of a substantially planar bottom surface of the present invention having micro-channels for defining individual, separate locations on a substantially planar bottom surface.

Figure 6:
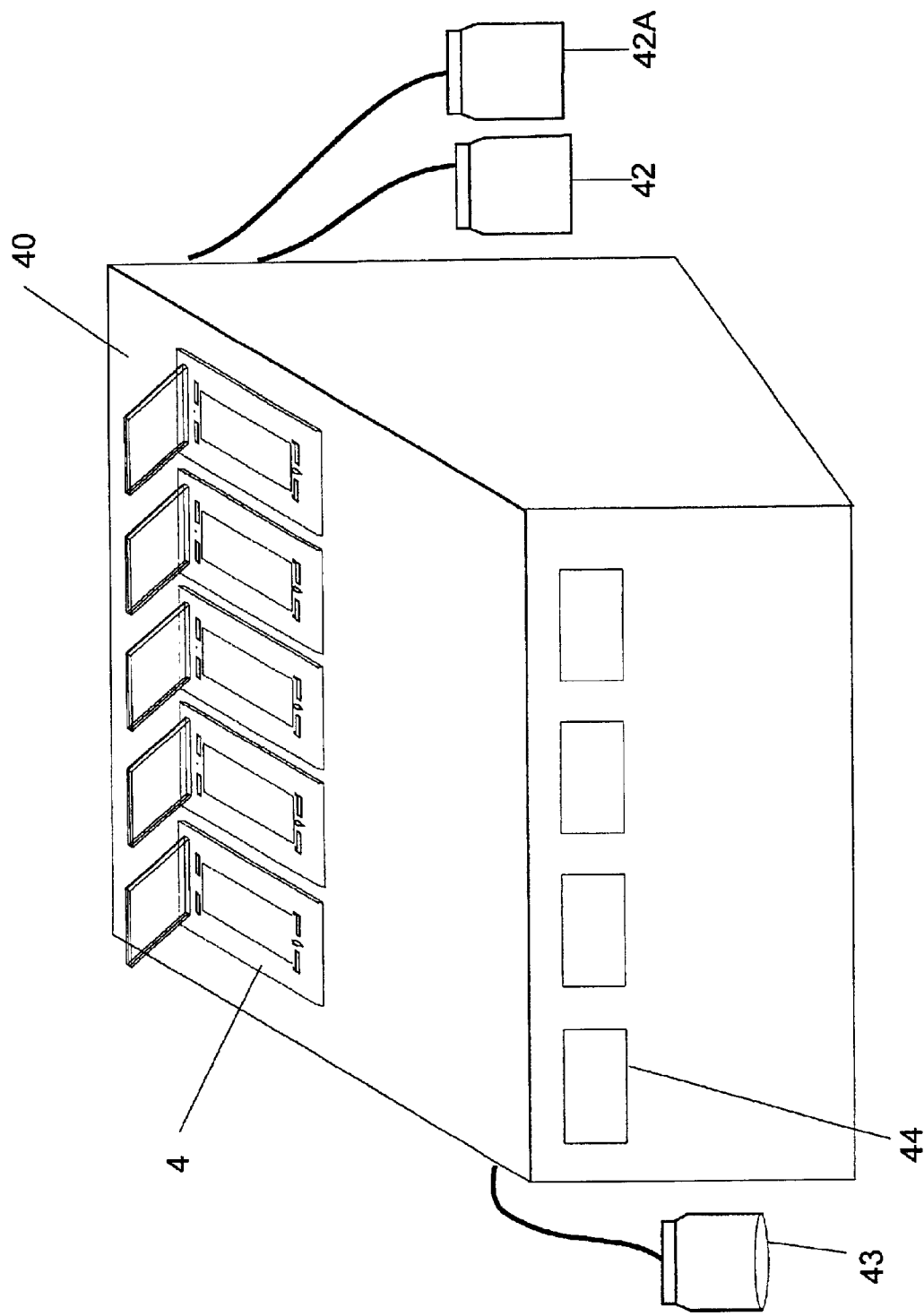

FIG. 6 provides a representation of a hybridization station of the present invention in use as part of a hybridization system.

DEFINITIONS

The term "array" as used herein refers to a substrate having a plurality of binding agents stably attached to, i.e., immobilized on, its surface, where the binding agents may be spatially located across the surface of the substrate in any of a number of different patterns.

The term "binding agent" as used herein refers to any agent that is a member of a specific binding pair, where such agents include: polypeptides, e.g. proteins or fragments thereof; nucleic acids, e.g. oligonucleotides, polynucleotides, and the like, as well as other biomolecules, e.g., polysaccharides, etc.

The term "polymer" as used herein refers to any compound that is made up of two or more monomeric units covalently bonded to each other, where the monomeric units may be the same or different, such that the polymer may be a homopolymer or a heteropolymer. Representative polymers include peptides, polysaccharides, nucleic acids and the like, where the polymers may be naturally occurring or synthetic.

The term "peptide" as used herein refers to any compound produced by amide formation between a carboxyl group of one amino acid and an amino group of another group, where the amino acids may be naturally occurring or synthetic.

The term "oligopeptide" as used herein refers to peptides with fewer than about 10 to 20 residues, i.e. amino acid monomeric units.

The term "polypeptide" as used herein refers to peptides with more than 10 to 20 residues.

The term "protein" as used herein refers to polypeptides of specific sequence of more than about 50 residues.

The term "nucleic acid" as used herein refers to a polymer composed of nucleotides, e.g. deoxyribonucleotides or ribonucleotides, or compounds produced synthetically (e.g. PNA as described in U.S. Pat. No. 5,948,902 and the references cited therein) which can hybridize with naturally occurring nucleic acids in a sequence specific manner analogous to that of two naturally occurring nucleic acids.

The terms "ribonucleic acid" and "RNA" as used herein refers to a polymer composed of ribonucleotides.

The terms "deoxyribonucleic acid" and "DNA" as used herein refers to a polymer composed of deoxyribonucleotides.

The term "oligonucleotide" as used herein denotes single stranded nucleotide multimers of from about 10 to 100 nucleotides and up to 200 nucleotides in length.

The term "polynucleotide" as used herein refers to single or double stranded polymer composed of nucleotide monomers of generally greater than 100 nucleotides in length.

DETAILED DESCRIPTION OF THE INVENTION

Array hybridization devices and methods for their use are provided. The subject devices are characterized by having a substantially planar bottom surface, a cover, at least one fluid port and at least one adjustable spacing element for adjusting the spacing between an array and the bottom surface. In using the subject devices, an array is placed on the at least one adjustable spacing element in the chamber and the space between the array and the bottom surface is adjusted by moving the at least one adjustable spacing element. The adjusted array is contacted with at least one biological sample introduced into the chamber. The subject inventions find use in a variety of array-based applications, including nucleic acid array hybridizations.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a chamber" includes a plurality of such chambers and reference to "the array" includes reference to one or more arrays and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As summarized above, the subject invention provides devices and methods for hybridizing arrays of polymeric agents. The subject inventions can be used to hybridize a number of different types of arrays in which a plurality of distinct polymeric binding agents are stably associated with at least one surface of a substrate or solid support. The polymeric binding agents may vary widely, however polymeric binding agents of particular interest include naturally-occuring and synthetic biopolymeric molecules, such as peptides, nucleic acids, polysaccharides and the like, where peptides and nucleic acids are of particular interest in many embodiments.

As is known in the art, a variety of substrates may be used, including both flexible and rigid substrates and may be fabricated from a variety of materials known in the art including nylon, nitrocellulose, polypropylene, polyester films such as polyethylene terephthalate, silicon, glass, plastics and the like. In many embodiments, the substrate will be a microscope slide, as is known in the art. In certain embodiments, a plurality of arrays may be stably associated with one substrate. For example, a plurality of arrays may be stably associated with one substrate, where the arrays are spatially separated from some or all of the other arrays associated with the substrate.

In further describing the subject invention, the devices employed in the subject invention are described first in greater detail, followed by a detailed description of the subject methods.

DEVICES

Array Hybridization Chamber

As described above, the device of the present invention is an array hybridization chamber for hybridizing at least one array. Generally, the chamber includes a substantially planar bottom surface, at least one adjustable spacing element, a cover and at least one fluid port.

The chamber may take a variety of configurations, with the only limitations being that it be shaped to receive an array. In many embodiments, the hybridization chamber will assume a circular, square or rectangular shape. For example, in those embodiments where the at least one array is stably associated with a microscope slide, e.g., a 1"×3" glass microscope slide as is known in the art, the chamber will typically be similarly rectangularly shaped. Furthermore, the chamber may be manufactured from a variety of materials, where the bottom and cover of the chamber may be manufactured from different materials, but where such materials will not substantially interfere with the hybridization reagents or process. Examples of such materials may include, but are not limited to, plastics such as polytetrafluoroethylene, polypropylene, polystyrene, polycarbonate and blends thereof, stainless steel and alloys thereof, silaceous materials, e.g., glasses, and the like. As will be apparent to those of skill in the art, the hybridization chamber may be manufactured to be re-useable or single use.

The volume of the chamber is sufficient to receive and enclose the substrate which embodies at least one array, which substrate is to be placed into the chamber. As such, the volume may vary depending on the specific array substrate size to be placed therein. In many embodiments, the volume of the chamber per square inch of substrate surface area may range from about 0.25 to 10 mL, usually from about 0.5 to 5 ml. In certain embodiments, the width of chamber exceeds the width of the substrate present in the chamber by at least about 0.1", often by at least about 0.5", where the width of the chamber may exceed the width of the substrate by as much as 3" or greater, but often does not exceed the width of the substrate by more than about 2". In certain embodiments, the length of the chamber exceeds the length of the substrate by at least about 0.1", usually by at least about 0.5", where the length of the chamber may exceed the length of the substrate by as much as 3" or greater, but generally does not exceed the length of the substrate by more than about 2". For example, in the embodiment of a chamber designed for a 1"×3" slide, the chamber is capable of accommodating at least about 2 ml, usually at least about 4 ml and more usually at least about 5 ml, where in many embodiments the chamber is able to accomodate a volume as great as 40 ml or greater, but often the chamber is one that does not exceed about 30 ml, and more often does not exceed about 20 ml in volume. As such, in those embodiments where the chamber is designed to handle a 1"×3" slide, the width generally ranges from at least about 1.0 to 3.0 inches, usually about 1.1 to 2.0 inches, the length generally ranges from about 3.0 to 6.0, usually about 3.10 to 5.0 inches, and the height generally ranges from about 0.025 to 0.5, usually about 0.05 to 0.25 inches.

Generally, as bottom surface, which typically substantially planar, and a cover form the physical boundaries of the chamber, where at least one array is placed between the two for hybridization. As such, the substantially planar bottom surface is configured to receive an array thereon and is usually substantially smooth. In certain embodiments, the cover, the substantially planar bottom surface or the array placement area of the substantially planar bottom surface may be removed and replaced with another substantially planar bottom surface or placement area. For example, the bottom surface may be replaced with another type of surface which is better suited to accommodate different array shapes and sizes. Alternatively, the cover, bottom surface or array placement area may be replaced with another type of surface having micro-channels or grooves therein to provide for the introduction, often times simultaneously, of more than one sample, each being introduced into the chamber such that each sample remains segregated from the other(s) and which may be delivered to different portions of the substrate surface. For example, if the substrate includes a plurality of arrays on its surface, a plurality of samples can be introduced into respective channels and each sample can be delivered to a different portion of a substrate surface, i.e., a different array. Alternatively, micro-channels or grooves positioned in the substantially planar bottom surface may define separate, individual, discrete regions or locations on the bottom surface, where such discrete locations may substantially correspond to arrays on a substrate to be placed in the chamber. Accordingly, in this particular embodiment, the micro-channels or grooves act to cause the samples to remain isolated from each other by interrupting the capillarity between the array surface and the substantially planar surface. In addition to segregating samples, the grooves may also enable the air to vent easily. In many embodiments, the substantially planar bottom surface may further comprise a temperature regulation system, at least one mixing element, at least one drying element, at least one automation system and/or micro-channels as will be described in more detail below.

A feature of the substantially planar bottom surface is that it includes at least one adjustable spacing element. Usually, the substantially planar bottom surface will have at least two adjustable spacing elements and more usually at least three or four adjustable spacing elements. Initially, the at least one adjustable spacing element serves to guide and adjust the at least one array on the substantially planar bottom surface, and may perform other functions as well, as will be described in more detail below. By adjust is meant to arrange or orient the at least one array in the chamber, i.e., adjust the array relative to the bottom planar surface of the chamber, e.g., adjust the spacing between the at least one array and the substantially planar surface by moving the at least one adjustable spacing element, e.g., raising and/or lowering the at least one adjustable spacing element to raise and/or lower the at least one array thereon. For example, the at least one array may be lowered to be brought into closer proximity with the bottom surface or may be raised to bring the at least one array into closer proximity to the cover.

Regardless of whether the at least one array is raised or lowered, the at least one adjustable spacing element is operatively associated with an actuating means. As will be appreciated by those of skill in the art, the at least one adjustable spacing element may be adjusted manually or automatically by association with an automation element. In instances when the at least one adjustable spacing element is activated automatically, the actuating means for raising or lowering the at least one adjustable spacing element may optionally include a sensing element for sensing when the at least one array is in contact with the at least one adjustable spacing element. A variety of sensor types may be used, such as optical sensors, thermal sensors and the like.

The at least one adjustable spacing element may be manufactured from a variety of materials, where such materials will not adversely effect the at least one array thereon or the hybridization process. Suitable materials include, but are not limited to, elastomers, i.e., rubber, polymers, e.g., plastics, stainless steel and alloys thereof, and the like. In many embodiments, the at least one adjustable spacing element will comprise a fluid impermeable layer for preventing substantial fluid contact with the at least one adjustable spacing element, where such impermeable layer facilitates cleaning of the at least one adjustable spacing element and the chamber, in many instances for re-use of the chamber. A variety of materials may be used for the fluid impermeable layer, including, but not limited to, elastomers, i.e., rubber, flexible polymers, and the like.

The at least one adjustable spacing element may be any shape such as round, rectangular, square, and the like and may be a variety of sizes, with the only limitation being that the at least one adjustable spacing element be sized and shaped so as not to substantially interfere with the at least one array placed thereupon shaped as a rectangle, square, circle, etc. As such, the at least one adjustable spacing element will typically be significantly smaller than the at least one array placed thereupon, where such size will vary depending on the specific substrate and array to be placed thereon. In those embodiments where the at least one adjustable spacing element has a square or rectangular configuration, the width of the portion contacting the array substrate generally ranges from about 0.015 to 0.15 inches, usually about 0.020 to 0.1 inches, the length may be as small as about 0.020 inches and as long as either the length or width of the substrate. In addition, the at least one adjustable spacing element may include means to anchor the substrate to the at least one spacer element, e.g., spring clips, clamps, vacuum, and the like. Alternatively but less desirably, the at least one spacing element is located on the opposite side of the substrate from the array side. In this orientation, the at least one spacing element may cover the entire surface of the substrate. For example, a vacuum clamp may be attached to the cover of the chamber and attach to the substrate.

As described above, the at least one adjustable spacing element may be oriented on the substantially planar bottom surface such that at least one array may be placed thereupon, typically such that the at least one array can be centered substantially in the middle of the substantially planar bottom surface, e.g., in an array placement area. For example, the at least one adjustable spacing element may be located around the periphery of the array placement area, e.g., at least two adjustable spacing elements may be positioned on two opposing sides of the array placement area or at least four adjustable spacing elements may be positioned on four sides of the array placement area, such that the edges of the array substrate rest on at least one adjustable spacing element without substantially interfering with the at least one array. By edges is generally meant those portions of the substrate not stably associated with a polymeric binding agent.

The substantially planar bottom surface of the chamber may also optionally include at least one fluid port for the ingress and egress of fluids such as washing agents, buffers and the like. As will be apparent to those of skill in the art, the at least one fluid port may be positioned in an alternative area of the chamber, for example the cover, etc. Typically, the chamber will be comprised of at least two fluid ports, e.g., a first fluid port for ingress of fluid and a second fluid port for egress of fluid, e.g., waste. In many embodiments, the at least one fluid port also enables the ingress and egress of at least one biological sample to into the chamber. However, typically a separate sample introduction element will be present so as to avoid contamination. In those embodiments where a plurality of samples are to be introduced into the chamber, often times simultaneously, the chamber, e.g., the bottom or the cover, will usually include a plurality of sample introduction means or fluid ports operatively associated with discrete regions or locations on the substantially bottom surface. The at least one adjustable spacing element is capable of changing the spacing of between the array and chamber opposing surfaces when the array is present in the chamber, e.g., the array surface and the opposing bottom surface of the chamber or the array surface and the opposing surface of the cover, where the magnitude of the spacing change that is achievable via the at least one adjustable spacer typically ranges from about 5 to 5000 microns, usually from about 05 to 2500 microns. In many embodiments, the at least one adjustable spacer element is capable of adjusting the distance between the array surface and opposing chamber surface from a first distance that provides for holding a fluid, particularly a fluid film, between the opposing chamber and array surfaces by surface tension to a second distance that does not provide for maintenance of a fluid between the opposing surfaces by surface tension. The variance in distance that the adjustable spacer must be able to provide in these embodiments necessarily depends on the nature of the fluid that is to be held between the opposing surfaces by surface tension. For aqueous fluids having a viscosity that does not differ from pure water by more than about 10%, the adjustable spacer is, in many embodiments, one that is capable of varying the distance between the opposing surfaces by a value ranging from about 5 to 5000 microns, usually from about 5 to 2500 microns.

The at least one fluid port is operatively associated with at least one fluid reservoir or vessel having washing agent, buffer and the like and usually it is associated with at least two reservoirs where one is used as a waste receptacle. Accordingly, a fluid communication element such as a channel or tubing structure allows fluid communication between the fluid reservoir, waste receptacle and the chamber. As such, a valve element will typically be present to facilitate one-way travel of the fluids, e.g., will open to provide a fluid connection between the fluid reservoir and the chamber and will close to deny a fluid connection.

Typically, a valve will be operatively associated with a pumping system for transporting fluids through the system, e.g., a peristaltic pump, positive displacement pump, e.g., a syringe or the like. Alternatively, a gas-pressure fluid delivery system may be used. The valve element typically will further include an actuating means which, when activated, opens and closes the valve, usually automatically. In many embodiments, a sensor element will also be present to detect fluid levels to prevent under or over filling of the chamber.

The at least one fluid port may be advantageously configured to allow the delivery and/or removal into and out of the chamber while maintaining a closed environment. For example, the at least one fluid port may include a valve element, as described, which opens and closes only to allow for fluid transfer into and out of the chamber. Alternatively, the port may also comprise a sealing element, penetrable by a puncturing element such as a needle or the like, associated with the fluid communication element such that the sealing element is penetrated when fluid is to be delivered or removed from the system and, as such, forms a fluid-tight seal around the needle to prevent fluid leakage from the chamber. After fluid transfer, the needle is removed from the sealing element and the sealing element closes around the point of needle introduction to again form a fluid-tight seal.

As described above, the chamber also includes a cover operatively associated with the substantially planar bottom surface such that the cover forms a sealed enclosure with the bottom surface when the cover is in a closed position.

The cover may be associated with the bottom surface in a variety of ways, as will be apparent to one of skill in the art. In certain embodiments, the bottom surface and the cover may be manufactured as one unit, for example the bottom and cover may be injection molded or the like to form one piece having an array entry/exit portion. In many embodiments, the cover may be operatively associated with the substantially planar bottom surface with a hinge, pin, screw, latch, clip, etc. In other embodiments, the cover may simply snap onto the bottom, or vice versa. Typically, the cover opens and closes automatically by an actuating means operatively associated with an automation system.

Regardless of the type of association between the substantially planar bottom surface and the cover, the cover will typically form a substantially vapor tight seal with the substantially planar bottom surface when the two are contacted together in a closed position. By substantially vapor tight seal is meant that the chamber is capable of preventing substantial evaporation of the fluidic contents of the chamber during a hybridization process.

The cover may take a variety of configurations, with the only limitations being that it be shaped and sized to enable compatibility with a substantially planar bottom surface. In many embodiments, the cover will assume substantially the same shape as the planar bottom surface to which it is to be associated, e.g., the cover may be square, rectangular, circular, and the like, e.g., the cover may be rectangularly shaped to accommodate a rectangularly shaped planar bottom surface, etc.

Similarly, in many embodiments, the cover will be substantially the same size as the planar bottom surface to which it is to be associated. For example, in those embodiments where the chamber is designed to handle a 1"×3" slide, the width generally ranges from about 1.0 to 3.0 inches, usually about 1.0 to 2.0 inches, the length generally ranges from about 3.0 to 6.0, usually about 3.0 to 5.0 inches, and the height generally ranges from about 0.04 to 0.5, usually about 0.05 to 0.25 inches.

As described above, the cover may be manufactured from a variety of materials including plastics such as polytetrafluoroethylene, polypropylene, polystyrene, polycarbonate and blends thereof, stainless steel and alloys thereof, silaceous materials, e.g., glasses, and the like. In many embodiments, the cover is substantially clear to enable direct visualization of the array within the chamber.

Typically, a plurality of chambers will be associated with an array hybridization station, wherein such a station is capable of receiving or holding a plurality of chambers for the concurrent hybridization of a plurality of arrays. As such, a hybridization system, including a station, at least one automation system, one or more hybridization chambers, fluid reservoirs and an optional array transfer element, e.g., a robotic arm or the like, enables partial or full hybridization of one or more arrays contained in one or more hybridization chambers, typically automatically.

Temperature Regulation System

As described above, the chamber may further comprise a temperature regulation system to maintain the temperature within the hybridization chamber at optimized levels according to pre-selected temperature profiles. The temperature regulation system may be directly incorporated in the chamber or, alternatively, the entire chamber may be placed in an environment that reflects the desired temperatures, for example a temperature controlled compartment or water bath. In many embodiments, the temperature regulation system is incorporated directly into the chamber, for example, into the substantially planar bottom surface. Temperature regulation may be carried out using a variety of mechanisms to regulate the temperature of the chamber, i.e., heat and/or cool the hybridization chamber, including, but not limited to, a thermoelectric means, e.g., a Peltier heater/cooler and a thermo-fluidic means, e.g., channels or tubings which recirculate a temperature controlled fluid through the chamber, and the like.

Alternatively, the temperature regulation system may be a separate structure, apart from the chamber. For example, the temperature regulation system may include a heating/cooling block adjacent the chamber where the temperature of the chamber is regulated by thermal exchange across a shared wall or across a relatively short space, or may be a part of a hybridization station.

The temperature regulation system may also include mechanisms to preheat or precool fluid before it is introduced into the chamber. This may be accomplished by placing the fluid reservoirs into a fluid bath, wherein the temperature of the fluid bath may be regulated, for example by a mechanism described above. Alternatively, the fluid may be heated with, for example, heat exchange coils associated with a temperature regulation element as it travels from the reservoir to the chamber through channels, tubing or the like.

In certain embodiments, the device includes a means for ensuring that the temperature of the chamber remains within a certain range, e.g., a range suitable for binding reactions, e.g., nucleic acid hybridization assays. As such, the temperature may range from about 0 to 95° C., usually from about 4 to 70° C., and more usually from about 25 to 65° C. The temperature range maintenance element may include one or more components that ensure the maintenance of the chamber at the desired temperature range, where such components include heating/cooling elements, thermosensors and feedback elements, processors, etc.

Mixing Elements

The chamber may also include at least one mixing element for mixing the contents of the chamber, e.g., biological sample, washing agent, buffer, etc. Typically, at least one mixing element will be directly incorporated into the chamber, but may also be a separate structure operatively associated with the chamber, such as a laboratory-type mixing plate, upon which the chamber may be placed or, alternatively, a hybridization station may include at least one mixing element, where at least one chamber may be placed in or on the station for at least a portion of the hybridization process, as described. In those embodiments where at least one mixing element is directly incorporated into the chamber, it will typically be incorporated into the substantially planar bottom surface, however other locations within the chamber are possible as well.

A variety of mixing elements may be used to mix the fluidic contents of the chamber. In certain embodiments, the contents are mixed by movement of the at least one adjustable spacing element to adjust the at least one array thereupon, i.e., raise or lower the at least one array, thereby creating agitation of the fluid within the chamber. In those embodiments having at least two adjustable spacing elements, the at least two adjustable spacing elements may be individually activatable so as to create a see-saw motion of the array thereupon, thus agitating the fluid in the chamber.

In other embodiments, the at least one mixing element is comprised of at least one resistor which is activated, i.e., heated, to produce or nucleate at least one bubble in the fluid within the chamber, where the creation and dissipation of the at least one bubble creates agitation in the chamber fluid, see for example U.S. Pat. No. 6,186,659, the disclosure of which is herein incorporated by reference. In yet other embodiments, an ultrasonic element is activated to create vibrations in the chamber fluid. Still other embodiments may employ a recirculation pump to remove and reintroduce chamber fluid into and out of the chamber. Additional embodiments activate at least one roller or solenoid to agitate the chamber fluid, see for example U.S. Pat. No. 5,910,228, the disclosure of which is herein incorporated by reference.

Drying Element

The hybridization chamber may also include at least one drying element for drying the at least one array. The at least one drying element may be directly integrated with the chamber, e.g., the substantially planar bottom surface or cover of the chamber, or may be a separate structure. In either case, the at least one drying element, e.g., gas jet(s), will be associated with a gas source, typically a gas that won't substantially interfere with the hybridization, e.g., dry Nitrogen, clean dry air, Argon, Xenon, and the like. The jet(s) function to expel a stream of gas onto or close to the at least one array for a predetermined period of time to dry the array, usually automatically at the end of the wash and/or hybridization processes.

Automation System

A feature of the hybridization chamber is that it may be optionally associated with an automation system capable of automating some or all of the various steps involved in the hybridization process. The automation system may be directly integrated in the hybridization chamber or may be a separated structure operatively associated with the chamber. In certain embodiments, more than one automation system may be present, e.g., at least two automation systems. In such an embodiment, a first automation system may be directly integrated in a hybridization chamber and a second automation element may be present in a separated structure operatively associated with the chamber, for example a hybridization station, wherein the two systems may work in concert. In this configuration, a chamber is capable of being automated both apart from a station, e.g., as a stand-alone chamber, and as part of a system when used with a hybridization station, for example when a plurality of chambers are hybridized on a station.

Regardless of whether the automation system is integrated into a hybridization chamber or a separate structure, such an automation system enables automated monitoring and control of some or all of the functions of hybridizing at least one array in a chamber according to a preprogrammed set of instructions. For example, an automation system may automatically monitor and control some or all of the following functions: opening and closing of the cover, moving the at least one adjustable spacing means to adjust an array thereupon, sample introduction, mixing of fluidic contents of the chamber, temperature regulation, fluid ingress and/or egress, etc. In certain embodiments, an automation system may be operatively associated with an array transfer element capable of automatically transferring one or more arrays to and from a first array station such as a carousel or the like and a respective chamber.

In many embodiments, the automation system generally carries out automation of the subject invention by an onboard processor contained within a hybridization chamber, a separate structure, e.g., a station or both. The onboard processor is typically appropriately programmed to operate the steps for hybridization as described herein according to an input set of process parameters. For example, the processor operates to provide appropriate instructions to each of the elements of the hybridization chamber or station according to a preselected time/temperature, mixing, humidity profile, e.g., fluid or valve operation, temperature sensor/controller operation, humidity operation, etc.

In some aspects, the chamber or station may be operatively associated with a keypad for direct entry of the desired profile into the onboard processor. Alternatively, the process parameters may be input by the user into a computer that is connected to the onboard processor, e.g., personal computer or the like. The computer will typically be programmed with appropriate script programs for the input of these various process parameters. In this configuration, the computer transmits the parameters entered in the script program to the onboard processor within the chamber or station, which then functions as described herein.

The automation means may be analogous to the means disclosed at column 12 to column 26 of U.S. Pat. No. 6,144,122, the disclosure of which is herein incorporated by reference.

The devices of the present invention will now be described in reference to the drawings.

FIG. 1 illustrates a schematic representation of a hybridization chamber 4 of the present invention. As described above, the chamber 4 comprises a substantially planar bottom surface 6 and a cover 8, herein shown in an open position. In this embodiment, the cover 8 is operatively associated with the substantially planar bottom surface 6 by a hinge or pin (not shown). Chamber 4 also includes an automation system (not shown), for automating some or all of the chamber's functions.

As described above, the substantially planar bottom surface is comprised of at least one adjustable spacing element. FIG. 1 shows the substantially planar bottom surface 6 with four adjustable spacing elements 14 oriented around array placement area 10. Substantially planar bottom surface 6 further comprises fluid port 16 and sample introduction means 18. In this particular embodiment, fluid port 16 serves both as a fluid ingress port and a fluid egress port. However, as described above, other embodiments may include a second fluid port for fluid egress, i.e., waste.

FIG. 2 illustrates another embodiment of the chamber 4, wherein the bottom surface 6 and the cover 8 are one unit with an array entry portion 20, through which at least one array may be inserted.

FIG. 3 shows another embodiment of a substantially planar bottom surface 7. In this embodiment, similar to FIG. 1, bottom surface 50 comprises two adjustable spacing elements 52, fluid ingress port 54, fluid egress port 56 and sample introduction means 58. Bottom surface 50 further includes at least one mixing element 60, where the at least one mixing element 60 may be at least one resistor, ultrasonic element, recirculation pump, at least one roller or at least one solenoid. In this embodiment, mixing element 60 is shown above the surface of the bottom surface 50, positioned in the array placement area 62. However, it is conceivable that the at least one mixing element 60 may be positioned in other locations of the bottom surface 50, for example within the bottom surface 50, e.g., under the surface and/or in areas other than the array placement area 62 or, alternatively, in or on the cover 8. Substantially planar bottom surface 50 also includes temperature regulation system 64 for monitoring and controlling the temperature of a chamber. Similar to a mixing element, temperature regulation system 64 may be positioned elsewhere, e.g., in or on the bottom surface 50 or in or on the cover 8. Drying elements 66, e.g., gas jets, are also positioned on the substantially planar bottom surface 50 for drying the at least one array, but may be positioned elsewhere as well, e.g., in or on the cover 8.

FIG. 4 shows another embodiment of the substantially planar bottom surface 76. In this embodiment, the array placement area has micro-channels 72 or grooves therein to provide for the segregated introduction of more than one sample through individual sample introduction means 74, often times simultaneously.

FIG. 5 illustrates yet another embodiment of the present invention wherein a plurality of samples can be introduced into the chamber, e.g., simultaneously, and which samples can then remain segregated from other sample. In the embodiment illustrated by FIG. 5, the array placement area 104 includes grooves or micro-channels 100 which define individual, separate, discrete array locations 102, herein shown as ten discrete locations, but in many embodiments there may be greater or fewer than ten discrete locations. Regardless of the number of locations, grooves 100 define discrete locations 102, where such locations substantially correspond or align with respective arrays on a substrate (not shown). For example, in this particular embodiment, the ten discrete array locations 102 would align with ten arrays on a substrate. The grooves 100 serve to disrupt the capillary action between different arrays on a substrate, thereby preventing sample introduced to one array location on a substrate from wicking or moving by capillary action to another array location on the substrate. Accordingly, each array location 102 has a respective fluid port 106 for sample introduction and or other for the ingress of other fluids. In certain embodiments fluid is removed from the chamber by fluid exit port 108 or, alternatively, each array location 102 may also include a separate fluid egress port (not show) or may remove fluid through respective fluid ingress ports 106. As described above for other embodiments, at least one mixing element (not shown) may also be operatively associated with the discrete location 102.

FIG. 6 shows an array hybridization station 40 operatively associated with two fluid reservoirs 42 and 42A, including, for example, wash buffer or the like and waste reservoir 43. Station 40 includes an automation system (not shown) for automating some or all of the functions of a hybridization process, usually for a plurality of hybridization chambers.

Hybridization station 40 is shown having optional liquid crystal displays (LCDs) 44 for the display of various process parameters such as time, temperature, humidity and process step. A hybridization system, including hybridization station 40, fluid reservoirs 42 and 42A and waste reservoir 43 and hybridization chamber 4, is shown processing five hybridization chambers 4 thereon; however, station 40 may typically accommodate 1–60 chambers or more, more typically 1–50 chambers concurrently. As will be apparent to those of skill in the art, hybridization chamber 4 may be positioned within hybridization station 40, instead of being positioned on top.

SYSTEMS

As mentioned above, the subject invention also includes a hybridization system capable of the partial or full hybridization of one or more arrays contained in one or more hybridization chambers, typically automatically. Accordingly, the hybridization system includes a hybridization station, at least one automation element, one or more hybridization chambers, fluid reservoirs and an optional array transfer element, e.g., a robotic arm or the like, as mentioned above.

An example of such a hybridization system is shown in FIG. 6, as described above. FIG. 5 illustrates a hybridization system having a hybridization station 40, fluid reservoirs 42 and 42A, waste reservoir 43 and at least one hybridization chamber 4.

METHODS

In practicing the subject inventions, the first step is to place at least one array onto at least one adjustable spacing element of a hybridization chamber of the present invention. In those embodiments where the at least one spacing element lowers the at least one array to be in closer proximity to the bottom, the array is placed such that the array-side of the substrate is facing the substantially planar bottom surface. In other embodiments where the at least one spacing element lifts the at least one array to be in closer proximity to the cover, the array is placed such that the array side of the substrate is facing the cover.

Once the at least one array has been placed on at least one adjustable spacing element, the at least one array is then adjusted in the chamber, where such adjustment comprises moving the at least one adjustable spacing element to adjust the spacing between the array and the substantially planar bottom surface, e.g., raising the at least one array to increase the spacing or lowering it to decrease the spacing, to create a capillary dimension between the at least one array and the bottom surface of the chamber or between the at least one array and the cover of the chamber so that a biological sample is moved through the capillary dimension area between the at least one array surface and the substantially planar bottom surface or the cover by capillary action. By capillary dimension is meant a gap or space of about 10–1500 microns, usually about 25–200 microns and more usually about 50–100 microns.

Next, at least one biological sample is introduced into the chamber through a fluid port or sample introduction means, where a variety of different samples may be used, e.g., physiological samples such as urine, tears, saliva, blood and blood fractions are particularly well suited for use with the present invention. In those embodiments where the sample is derived from a physiological source, i.e., a biological source, the physiological source may be derived from a variety of eukaryotic sources, with physiological sources of interest including sources derived from single-celled organisms such as yeast and multicellular organisms, including plants and animals, particularly mammals, where the physiological sources from multicellular organisms may be derived from particular organs or tissues of the multicellular organism, or from isolated cells derived therefrom. In obtaining the sample of interest from the physiological source from which it is derived, the physiological source may be subjected to a number of different processing steps, where such processing steps might include tissue homogenization, cell isolation and cytoplasm extraction, nucleic acid extraction and the like, where such processing steps are known to those of skill in the art. For example, methods of isolating RNA from cells, tissues, organs or whole organisms are known to those of skill in the art and are described in Maniatis et al. (1989), Molecular Cloning: A Laboratory Manual 2d Ed. (Cold Spring Harbor Press).

As will be apparent to those of skill in the art, the sample may be any sample which includes a member of a specific binding pair, i.e., a target biomolecule, i.e., a sample capable of hybridizing with the binding agent(s) of the at least one array, e.g., peptides and nucleic acids are of particular interest. Typically, the sample includes the target biomolecule, often pre-amplified and labeled, e.g., nucleic acid and a hybridization buffer, e.g., salts, surfactants and the like.

If sample is introduced manually, the sample is pipetted or introduced into a sample introduction means or to the edge of the slide where it is then drawn or wicked between the substantially planar bottom surface or cover and the substrate. For example, if the at one array has been lowered by the at least one adjustable spacing element to create a capillary dimension between the at least one array and the bottom surface, sample will be introduced and wicked between the two. Alternatively, if the at one array has been raised by the at least one adjustable spacing element to create a capillary dimension between the at least one array and the cover, sample will be introduced and wicked between the at least one array and the cover. If the sample is to be introduced automatically, the sample is then automatically introduced through a fluid port or sample introduction means between either the array and a bottom surface or a cover of the chamber, as described above.

Once the at least one array is adjusted in the chamber and the sample is introduced whether manually or automatically, the cover of the chamber is closed, usually automatically, to form a sealed enclosure with the bottom surface, typically forming a substantially vapor tight seal which prevents substantial evaporation of the fluidic contents of the chamber. Alternatively, if the bottom and cover are manufactured as one unit, the array entry portion of the chamber is sealed to form a sealed enclosure and typically to form a substantially vapor tight seal. As will be apparent, the cover may be closed either after the sample has been introduced, as described, or before. Typically, if the sample is introduced manually, the cover will be closed after the sample is introduced and if the sample is introduced automatically, the cover will be closed before.

As described above, the spacing, i.e., the capillary dimension, between the at least one array and the substantially planar bottom surface or the cover enables a sample to be wicked across the surface of the at least one array by capillary action, thus enabling effective even distribution of the sample over the at least one array surface. As mentioned above, multiple samples may be introduced via separate sample introduction means or fluid ports into segregated micro-channels of the invention. Regardless of how many samples are introduced, i.e., whether one or more samples are introduced into the chamber, a sample is substantially contained between the array surface and the substantially planar surface or cover by capillary forces. In other words, there are no side walls retaining or holding the fluid, but the fluid is retained or held between the at least one array surface and a boundary or surface of the chamber, e.g., between the at least one array surface and the bottom of the chamber or between the at least one array surface and the cover of the chamber. Accordingly, the volume of sample maintained between the at least one array surface and the bottom or cover is determined by the spacing or distance between the substantially planar surface or cover and the at least one array. The sample is thus bounded by either the edges of the substrate or the geometry of the planar surface. For example, if the planar surface is smaller than the substrate, the fluid will be bounded by the edges of the planar surface. Alternatively, in those embodiments where the substantially planar bottom surface includes individual array locations separated by grooves, as described above, the samples are thus bounded by the grooves. As such, no sealing means in contact with the array is required.

In many embodiments, the biological sample may optionally be mixed with the at least one array with a mixing element, as described above, to minimize processing times. After optional mixing, the sample is allowed to incubate with the at least one array. It will be apparent to those of skill in the art that the sample may be mixed throughout the entire incubation cycle or periodically throughout the incubation cycle. Incubation cycle times may vary depending on the particular binding pairs, but in those embodiments involving nucleic acid hybridization for the purpose of expression profiling, the incubation time is at least about 1 to 48 hours, usually about 3 to 24 hours, and more usually about 5 to 17 hours. The incubation time for polymorphism analysis or other assays in which the sample has been subjected to polymerase chain reaction or other means to yield high concentrations of target molecules may be as short as 1 to 60 minutes.

Typically, the temperature of the chamber will be monitored and adjusted to an optimal hybridization temperature. Temperatures may vary depending on the particular binding pair, but in those embodiments involving nucleic acid hybridization, the temperature is at least about 25 to 70° C., usually about 30 to 65° C., and more usually about 35 to 65° C. The temperature regulation system may be activated at any point in the hybridization process, for example before the at least one array is placed in the chamber or after sample introduction. Similarly, a humid environment may be provided and maintained at any point in the process and may remain constant or variable throughout. If such a humid environment is desired, fluid may be introduced into the chamber, usually in segregated micro-channels or the like, to provide and maintain an optimum humidity level in the chamber, e.g., usually about a 70–100% humidity level and more usually about a 90–100% humidity level.

Once the hybridization reaction is complete, unreacted sample is removed from the chamber and the chamber is typically washed with at least one cycle of a washing agent to remove unbound and non-specifically bound sample from the chamber, generally at least two wash cycles are used. Washing agents used in array hybridization chambers are known in the art and, of course, may vary depending on the particular binding pair used in the particular hybridization process. For example, in those embodiments employing nucleic acid hybridization, washing agents of interest include, but are not limited to, salt solutions such as SSPE or SSC, as is known in the art, at different concentrations and may include some surfactant as well.

So as not to dry-out the array while the fluids are being exchanged, typically the at least one array will be further adjusted by the at least one adjustable spacing element to trap a portion of the first fluid, e.g., biological sample, under the at least one array, i.e., between the at least one array, i.e., the at least one array surface side of the substrate, and the substantially planar bottom surface or the cover. While retaining the trapped portion of the first fluid in the chamber, substantially all of the unstrapped portion of the first fluid may be removed from the chamber and a second fluid may be introduced, thereby exchanging a plurality of fluids in the chamber while preventing drying-out of the at least one array.

In many embodiments, the washing agent may also be mixed with the at least one array with a mixing element, as described above. After the final wash has been completed, the array is further adjusted to decrease the capillary forces. For example, in those embodiments where the sample was retained between the at least one array and the substantially bottom surface, the at least one array will then be lifted, usually to its highest position, to minimize the capillarity on the fluid so that all of the fluid can then be removed from the chamber. Alternatively, in those embodiments where the sample was retained between the at least one array and the cover, the at least one array will then be lowered to minimize the capillarity on the fluid so that all of the fluid can then be removed from the chamber.

After the biological sample has been removed from the chamber and the at least one array has been washed, the at least one array may be dried. In certain embodiments, at least one gas jet which expels a gas over or near the at least one array is activated to dry the at least one array. A multitude of gases are suitable for use with the subject invention and include, but are not limited to clean dry air, Nitrogen, Argon, Xenon, and the like.

Alternatively, the at least one adjustable spacing element may be set to an intermediate position to control or minimize the capillary forces on the fluid so that the fluid may then be removed from the chamber slowly. Accordingly, as a meniscus sweeps across the at least one array surface, all fluid is entrained and is thus removed, leaving the array surface substantially dry.

As will be appreciated, the above described methods may be substantially automated by the activation of at least one automation system.

In many embodiments, a plurality of chambers having at least one array therein are processed or hybridized concurrently, for example in association with a hybridization station, wherein some or substantially all of the processing is automated.

It is evident from the above results and discussion that the above described invention provides methods and devices for array hybridization which are simple to use, efficient, at least partially automated and can be used with a multitude of different array formats. The above described invention provides for a number of advantages, including the even distribution of a sample over an array surface, the introduction of more than one sample to different areas of an array substrate and the substantial prevention of dehydration of the array surface during the hybridization process. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An array hybridization chamber comprising:
    a. a bottom surface for receiving at least one array to be hybridized and a cover operatively associated with said bottom surface, wherein said cover forms a sealed enclosure with said bottom surface when in a closed position,
    b. at least one adjustable spacing element positioned on said bottom surface for adjusting the spacing between said at least one array and said bottom surface and said cover when said bottom surface and said cover are operatively associated,
    c. at least one fluid port for delivering and/or removing fluid from said chamber.

2. The array hybridization chamber according to claim 1, wherein said chamber comprises at least two adjustable spacing elements.

3. The array hybridization chamber according to claim 1, wherein said cover is operatively associated with said substantially planar bottom surface by a hinge.

4. The array hybridization chamber according to claim 1, wherein said cover forms a substantially vapor tight seal with said substantially planar bottom surface when in a closed position.

5. The array hybridization chamber according to claim 1, further comprising at least one mixing element for mixing the contents of said chamber.

6. The array hybridization chamber according to claim 5, wherein said at least one mixing element is selected from the group consisting of at least one resistor, ultrasonic element, recirculation pump, at least one roller, at least one adjustable spacing element and at least one solenoid.

7. The array hybridization chamber according to claim 1, further comprising a temperature regulation system for monitoring and controlling the temperature of said chamber.

8. The array hybridization chamber according to claim 7, wherein said temperature regulation system is selected from the group consisting of a thermo-electric means, a thermo-fluidic means and a heating/cooling block.

9. The array hybridization chamber according to claim 1, further comprising a system for automating at least a portion of said array hybridization chamber.

10. A system for array hybridization, said system comprising:
    (a) a hybridization station, and
    (b) at least one hybridization chamber according to claim 1.

11. The system according to claim 10, wherein said system further comprises an automation system for automating at least a portion of a hybridization process.

12. The system according to claim 10, further comprising an array.

13. An array hybridization chamber according to claim 1, further comprising an array.

14. An array hybridization chamber comprising:
    a. a bottom surface for receiving at least one array to be hybridized and comprising a plurality of microchannels for introducing a plurality of biological samples into said chamber, such that said plurality of samples remain segregated from each other, b. at least one adjustable spacing element for adjusting the spacing between said at least one array and said bottom surface, c. a cover operatively associated with said bottom surface, wherein said cover forms a sealed enclosure with said bottom surface when in a closed position, and d. at least one fluid port for delivering and/or removing fluid from said chamber.

15. The array hybridization chamber according to claim 14, wherein said micro-channels define discrete locations on said substantially planar bottom surface.

16. The array hybridization chamber according to claim 14, wherein said chamber comprises at least two adjustable spacing elements.

17. The array hybridization chamber according to claim 16, wherein said at least one drying element comprises at least one gas jet.

18. The array hybridization chamber according to claim 14, wherein said cover is operatively associated with said substantially planar bottom surface by a hinge.

19. The array hybridization chamber according to claim 14, wherein said cover forms a substantially vapor tight seal with said substantially planar bottom surface when in a closed position.

20. The array hybridization chamber according to claim 14, further comprising at least one mixing element for mixing the contents of said chamber.

21. The array hybridization chamber according to claim 20, wherein said at least one mixing element is selected from the group consisting of at least one resistor, ultrasonic element, recirculation pump, at least one roller, at least one adjustable spacing element and at least one solenoid.

22. The array hybridization chamber according to claim 14, further comprising a temperature regulation system for monitoring and controlling the temperature of said chamber.

23. The array hybridization chamber according to claim 22, wherein said temperature regulation system is selected from the group consisting of a thermo-electric means, a thermo-fluidic means and a heating/cooling block.

24. An array hybridization chamber comprising:

a. a bottom surface for receiving at least one array to be hybridized, b. at least one adjustable spacing element for adjusting the spacing between said at least one array and said bottom surface, c. a cover operatively associated with said bottom surface, wherein said cover forms a sealed enclosure with said bottom surface when in a closed position, d. at least one fluid port for delivering and/or removing fluid from said chamber, and e. at least one drying element for drying said at least one array.

25. The array hybridization chamber according to claim 24, wherein said chamber comprises at least two adjustable spacing elements.

26. The array hybridization chamber according to claim 24, wherein said cover is operatively associated with said substantially planar bottom surface by a hinge.

27. The array hybridization chamber according to claim 24, wherein said cover forms a substantially vapor tight seal with said substantially planar bottom surface when in a closed position.

28. The array hybridization chamber according to claim 24, further comprising at least one mixing element for mixing the contents of said chamber.

29. The array hybridization chamber according to claim 28, wherein said at least one mixing element is selected from the group consisting of at least one resistor, ultrasonic element, recirculation pump, at least one roller, at least one adjustable spacing element and at least one solenoid.

30. The array hybridization chamber according to claim 24, further comprising a temperature regulation system for monitoring and controlling the temperature of said chamber.

31. The array hybridization chamber according to claim 30, wherein said temperature regulation system is selected from the group consisting of a thermo-electric means, a thermo-fluidic means and a heating/cooling block.

* * * * *